United States Patent [19]

Inbasekaran et al.

[11] Patent Number: 4,806,688
[45] Date of Patent: Feb. 21, 1989

[54] PREPARATION OF DIAMINO- AND DIALKYLAMINOBENZENEDIOLS

[75] Inventors: Muthiah N. Inbasekaran; Robert M. Strom, both of Midland, Mich.

[73] Assignee: The Dow Chemical Company, Midland, Mich.

[21] Appl. No.: 864,063

[22] Filed: May 16, 1986

[51] Int. Cl.[4] .............................................. C07C 85/24
[52] U.S. Cl. .................................... 564/443; 564/384
[58] Field of Search ............................... 564/443, 384

[56] References Cited

U.S. PATENT DOCUMENTS 3,557,159  1/1971  Gruber ................................. 260/396
3,681,403  8/1972  Somlo et al. ......................... 260/396

OTHER PUBLICATIONS

Augustine, R. L., *Catalytic Hydrogenation*, Marcel Dekkes Inc., New York (1965), p. 128.
Baltzly, R. et al., "The Catalytic Hydrogenolysis of Halogen Compound", *J. Am. Chem. Soc.*, vol. 68, pp. 261–265 (1946).
Rylander, P., *Catalytic Hydrogenation in Organic Syntheses*, Academic Press, New York (1979) pp. 235, 236, 249.
Kirk–Othmer, *Encyclopedia of Chemical Technology*, 3d ed., vol. 2, pp. 422, 425, 430–431.
Marxer, A., *Helvetica Chimica Acta*, vol. 39, No. 38, pp. 335–340.

*Primary Examiner*—Glennon H. Hollrah
*Assistant Examiner*—John A. Sopp

[57] ABSTRACT

Prepare diamino- or dialkylaminobenzenediols by hydrogenating benzoquinone compounds in the presence of a solvent and a catalyst.

25 Claims, No Drawings

PREPARATION OF DIAMINO- AND DIALKYLAMINOBENZENEDIOLS

BACKGROUND OF THE INVENTION

This invention relates to the hydrogenation of benzoquinone compounds. More specifically, it pertains to a process for the hydrogenation of diaminodihalo- and dialkylaminodihalobenzoquinones to produce diamino- and dialkylaminobenzenediols.

Diamino- and dialkylaminobenzenediols are useful as monomers in the preparation of polybenzoxazoles (PBO). Polybenzoxazoles can be prepared by reacting certain benzenediols with bisacids, bisacid halides, bisesters or bisnitriles. Polybenzoxazole fibers have high tensile strength and thermal stability and are desirable for military, aerospace and other applications requiring rigid materials.

The known methods for preparing the benzenediol monomers typically involve a multi-step synthesis wherein expensive reagents are required and overall yield is poor. For example, one method involves oxidative bishydroxylation of hydroquinone with hydrogen peroxide and an alkali to produce 2,5-dihydroxy-p-benzoquinone. The reaction of hydrogen chloride and methanol with the dihydroxybenzoquinone yields 2,5-dimethoxy-p-benzoquinone which is aminated with ammonia and then reduced with stannous chloride in concentrated hydrochloric acid to give 2,5-diamino-1,4-benzenediol with an overall yield of only about 20 percent. See R. Wolf, M. Okada and C. S. Marvel, *J. Polymer Science*, Part A, 6, 1503 (1968).

A direct reduction of 2,5-diamino-1,4-benzoquinone with stannous chloride and HCl to produce 2,5-diamino-1,4-benzenediol is described in Beilstein's *Handbuch der Organischen Chemie*, 4th ed., Main Work, V. 13, p. 791. This process suffers from the fact that the diaminobenzoquinone starting material is not readily commercially available but must be prepared from the cheaper hydroquinone by the multi-step process mentioned above. Other methods involve the reduction of a dihalodiaminobenzoquinone to the corresponding dihalodiaminohydroquinone without the elimination of the halogen substituents. See, e.g., U.S. Pat. No. 4,337,196; Brit. 1,130,275 and Fr. 1,544,504.

A simple economical process is needed that would provide a high yield and allow both the reduction of the benzoquinone and the elimination of the halogen substituents. Such a process would allow the effective production of diamino- and dialkylaminobenzenediol monomers for use in preparing the highly desirable polybenzoxazoles.

SUMMARY OF THE INVENTION

The present invention is such a straightforward and inexpensive one-step process that provides a high yield of diamino- and dialkylaminobenzenediols. This process comprises contacting, under reaction conditions, a readily available diaminodihalo- or dialkylaminodihalobenzoquinone and a hydrogenating agent in the presence of a solvent and a noble metal-containing catalyst. It has surprisingly been found that the use of a noble metal-containing catalyst in the present invention results in a high yield and provides for reduction of the benzoquinone and elimination of the halogen substituents.

The diamino- and dialkylaminobenzenediols so produced can be condensed with bisacids, bisacid halides, bisesters or bisnitriles to produce poybenzoxazoles. Polybenzoxazole fibers have high tensile strength and thermal stability and hence have great potential for various industrial applications.

DETAILED DESCRIPTION OF THE INVENTION

According to the process of the present invention, the benzoquinone starting material is contacted with a hydrogenating agent in the presence of a solvent and a catalyst. The preferred benzoquinone compounds used as the starting material in the present invention correspond to the following general formula:

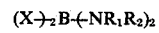

wherein B is 1,4-benzoquinone, each X is independently chloro, bromo, fluoro or iodo, most preferably chloro, and $R_1$ and $R_2$ independently can be hydrogen, $C_{1-10}$ alkyl or benzyl, most preferably hydrogen.

Typical benzoquinone compounds include 2,5-dichloro-3,6-diamino-1,4-benzoquinone, 2,5-dibromo-3,6-diamino-1,4-benzoquinone, 2,5-dichloro-3,6-dibenzylamino-1,4-benzoquinone, 2,5-dichloro-3,6-dimethylamino-1,4-benzoquinone, 2,5-dichloro-3,6-diethylamino-1,4-benzoquinone, with 2,5-dichloro-3,6-diamino-1,4-benzoquinone, 2,5-dichloro-3,6-dimethylamino-1,4-benzoquinone and 2,5-dichloro-3,6-dibenzylamino-1,4-benzoquinone being preferred. The most preferred benzoquinone starting material is 2,5-dichloro-3,6-diamino-1,4-benzoquinone. These benzoquinone starting materials can be prepared by methods well-known in the art. The typical preparation usually involves the reaction of excess ammonia or ammonium hydroxide with tetrahaloquinone. See, e.g., U.S. Pat. No. 4,337,196.

A catalyst is advantageously employed in the practice of the present invention. The hydrogenation catalyst can be any material which contains a noble metal and will catalyze the conversion of the benzoquinone starting material in the presence of a hydrogenating agent to the desired benzenediol. Examples of typical catalysts include noble metals on carbon, noble metal oxides, and noble metals supported on alkaline earth carbonates. Noble metals herein refer to gold, silver, platinum, palladium, iridium, rhodium, mercury, ruthenium and osmium. Preferred catalysts include palladium on carbon, platinum on carbon, and platinum oxide. The most preferred hydrogenation catalyst is palladium on carbon. The catalyst is employed in an amount which is sufficient to catalyze the conversion of starting material in the presence of a hydrogenating agent to the corresponding benzenediol. Typically, from about 0.0005 to about 0.1 molar equivalents of catalyst are present per equivalent of benzoquinone starting material. Preferably, from about 0.02 to about 0.05 equivalents of catalyst are present throughout the reaction.

A solvent is advantageously employed in the process of the present invention. Solvents employed in the process of the present invention preferably are compounds having at least one oxygen atom therein, such as, for example, water, ethers, esters, ketones, alcohols, and carboxylic acids. Specific examples of preferred solvents include water, methanol, ethanol, propanol, dimethylformamide and dioxane. Water is the most preferred solvent. Preferably, from about 1 to about 50 volumes of solvent are employed per volume of benzoquinone starting material. More preferably, from about 5 to about 10 volumes of solvent are employed.

Hydrogenating agents are well-known. The hydrogenating agent employed in the process of the present invention can be any material which will supply hydrogen to the reaction. Hydrogen gas and hydrazine are preferred in the process of the present invention. The hydrogenating agent is used in an amount sufficient to hydrogenate the benzoquinone starting material. When hydrogen is employed, the molar ratio of hydrogen gas to benzoquinone starting material is between about 3:1 and about 30:1. Preferably, about 5:1. Typically, from about 4 to about 8 molar equivalents of hydrazine are employed per equivalent of benzoquinone starting material. Preferably, from about 3 to about 6 molar equivalents of hydrazine are employed.

The process of the present invention can be carried out at any temperature and pressure at which the reaction will proceed. Preferably, the process is carried out at about 20° C. and about 100° C., most preferably between about 20° C. and about 50° C. The process can be carried out at sub- or superatmospheric pressures with atmospheric pressure being preferred for convenience. A total reaction time of from 4 to 72 hours is generally adequate to convert the starting material to the corresponding benzenediol.

Surprisingly, in the process of the present invention, the halogen atoms are removed from the benzoquinone ring system and the benzoquinone is converted to the corresponding benzenediol. As the halogen atoms are removed, a hydrogen halide is believed to be produced. While not wanting to be bound by any theory, it is believed that a unique feature of the present invention is the ability of the amino groups to capture the hydrogen halide as it is produced and thereby avoid acid poisoning of the catalyst. The presence of the amino groups apparently eliminates the need for the addition of external base as the reaction proceeds and thereby offers an added economic advantage. Furthermore, the hydrogen halide thus trapped by the amino groups apparently helps to stabilize the benzenediol and thereby avoids oxidative decomposition of the product. By avoiding catalyst poisoning and effectively stabilizing the final product, the amino groups appear to aid in generating surprisingly high yields.

The benzenediol compounds prepared by the process of the present invention correspond to the following general formula:

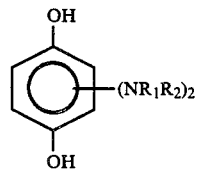

wherein $R_1$ and $R_2$ are as defined above. Typical benzenediols include 2,5-diamino-1,4-benzenediol, 2,5-dibenzylamino-1,4-benzenediol, 2,5-dimethylamino-1,4-benzenediol, 2,5-diethylamino-1,4-benzenediol, with 2,5-diamino-1,4-benzenediol, 2,5-dimethylamino-1,4-benzenediol and 2,5-dibenzylamino-1,4-benzenediol being preferred. The most preferred benzenediol is 2,5-diamino-1,4-benzenediol.

The product can be recovered using known recovery methods such as filtration, washing, etc. The product is generally isolated and stored as a hydrohalide salt in order to prevent oxidative decomposition. It is also suitable common practice to isolate the product as a salt of any mineral acid such as sulfuric, nitric or phosphoric acid. Typical yields of benzenediol are at least about 50 to 90 percent based on the benzoquinone starting material. Preferably, the yield will be at least about 70 percent. The maximum yields generally are obtained when hydrogen gas is directly applied.

SPECIFIC EMBODIMENTS

The following example is given to illustrate the invention and should not be construed as limiting its scope.

EXAMPLE 1

To a reaction vessel is added 24.6 g of 2,5-dichloro-3,6-diamino-1,4-benzoquinone, 1.6 g of 10 weight percent palladium on carbon and 300 ml of water. The mixture is vigorously stirred and hydrogen gas simultaneously is passed through the mixture for 48 hours at ambient temperature. The mixture is then filtered and washed with 50 ml of water. Then, 150 ml of concentrated hydrochloric acid is added, with cooling, to the filtrate. After 30 minutes, the white crystals are filtered, washed with small amounts of ethanol and ether, and suction dried. The yield of 2,5-diamino-1,4-benzenediol bishydrochloride is 87.3 mole percent (22.10 g) based on the benzoquinone starting material.

EXAMPLE 2

To a reaction vessel is added 23.5 g of 2,5-dichloro-3,6-dimethylamino-1,4-benzoquinone, 2.0 g of 10 weight percent palladium on carbon and 400 ml of water. The mixture is vigorously stirred and hydrogen gas simultaneously is passed through the mixture for 72 hours at ambient temperature. The mixture is then filtered and washed with 50 ml of water. Then, 200 ml of concentrated hydrochloric acid is added, with cooling, to the filtrate. After 30 minutes, the white crystals are filtered, washed with small amounts of ethanol and ether, and suction dried. The yield of 2,5-dimethylamino-1,4-benzenediol bishydrochloride is 85.0 mole percent (20.31 g) based on the benzoquinone starting material.

The examples demonstrate that the process of the present invention is a simple and efficient method capable of producing surprisingly high yields of diamino- and dialkylaminobenzenediols.

What is claimed is:

1. A process for the preparation of diamino- and dialkylaminobenzenediols comprising contacting a diaminodihalo- or dialkylaminodihalobenzoquinone with a hydrogenating agent in the presence of a solvent and a noble metal-containing catalyst under conditions such that the amine groups on the benzoquinone are not protonated when the reaction commences but the amine groups capture hydrogen halide produced as the reaction proceeds such that the corresponding benzenediol is produced.

2. The process of claim 1 wherein the benzoquinone starting material corresponds to the following general formula:

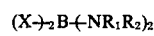

wherein B is 1,4-benzoquinone, X is chlorine, bromine, fluorine or iodine and $R_1$ and $R_2$ can be hydrogen, $C_{1-10}$ alkyl or benzyl.

3. The process of claim 2 wherein the hydrogenating agent is hydrogen gas.

4. The process of claim 2 wherein the hydrogenating agent is hydrazine.

5. The proccess of claim 2 wherein the solvent is an oxygen-containing compound.

6. The process of claim 2 wherein the catalyst is a noble metal supported on an alkaline earth carbonate.

7. The process of claim 2 wherein the catalyst is a noble metal supported on carbon.

8. The process of claim 3 wherein the benzoquinone starting material is 2,5-dichloro-3,6-diamino-1,4-benzoquinone.

9. The process of claim 3 wherein the benzoquinone starting material is 2,5-dibromo-3,6-diamino-1,4-benzoquinone.

10. The process of claim 3 wherein the benzoquinone starting material is 2,5-dichloro-3,6-dibenzylamino-1,4-benzoquinone.

11. The process of claim 8 wherein the solvent is water.

12. The process of claim 11 wherein the catalyst is palladium on carbon.

13. The process of claim 12 wherein from aobut 0.02 to about 0.05 equivalents of catalyst are present per mole of benzoquinone.

14. A process for the preparation of 2,5-diamino-1,4-benzenediol comprising passing hydrogen gas through a mixture of 2,5-dihalo-3,6-diamino-1,4benzoquinone, a noble metal-containing catalyst and a solvent, under conditions such that the amino groups on the benzoquinone are not protonated when the reaction commences but the amino groups cpature hydrogen halide produced as the reaction proceeds such that a 2,5-diamino-1,4-benzenediol is produced in a yield of greater than 70 percent based on the benzoquinone.

15. The process of claim 14 wherein the dihalodiaminobenzoquinone is 2,5-dichloro-3,6-diamino-1,4-benzoquinone.

16. The process of claim 15 wherein the solvent is water.

17. The process of claim 16 wherein the catalyst is palladium on carbon.

18. A process for preparing 2,5-diamino-1,4-benzenediol comprising the steps:
(a) passing hydrogen gas at about ambient temperature through a mixture comprising: (1) 2,5-dichloro-3,6-diamino-1,4-benzoquinone; (2) palladium on carbon; and (3) a solvent chosen such that the amino groups on the benzoquinone are not initially protonated; and
(b) stirring the mixture for a time sufficient to achieve substantial hydrogenation of the benzoquinone under reaction conditions such that hydrogen chloride generated in the reaction is substantially captured by the amine groups.

19. The process of claim 18 wherein the solvent is water.

20. The process of claim 19 wherein the 2,5-diamino-1,4 benzenediol is produced in a yield of greater than 70 percent based on the benzoquinone.

21. The process of claim 20 wherein the 2,5-diamino-1,4-benzenediol is produced in a yield of about 85 percent or greater, based upon the benzoquinone.

22. A process of claim 1 wherein the benzenediol produced corresponds to the general formula:

$$\underset{\text{OH}}{\overset{\text{OH}}{\bigcirc}}-(NR_1R_2)_2$$

wherein $R_1$ and $R_2$ are independently hydrogen, $C_{1-10}$ alkyl or benzyl.

23. A process of claim 1 wherein the catalyst comprises a noble metal on carbon, a noble metal oxide or a noble metal supported on alkaline earth carbonates.

24. A process of claim 1 wherein the catalyst comprises palladium on carbon, platinum on carbon or palladium oxide.

25. A process of claim 1 wherein the catalyst comprises palladium on carbon.

* * * * *